United States Patent
Bille

(10) Patent No.: US 7,611,244 B2
(45) Date of Patent: Nov. 3, 2009

(54) ADAPTIVE OPTICS FOR COMPENSATING FOR OPTICAL ABERRATIONS IN AN IMAGING PROCESS

(75) Inventor: Josef Bille, Heidelberg (DE)

(73) Assignee: Heidelberg Engineering GmbH, Heidelberg (DE)

( * ) Notice: Subject to any disclaimer, the term of this patent is extended or adjusted under 35 U.S.C. 154(b) by 367 days.

(21) Appl. No.: 11/562,902

(22) Filed: Nov. 22, 2006

(65) Prior Publication Data

US 2007/0103642 A1   May 10, 2007

Related U.S. Application Data

(63) Continuation-in-part of application No. 10/718,406, filed on Nov. 20, 2003, now Pat. No. 7,510,283.

(51) Int. Cl.
 *A61B 3/10* (2006.01)
 *A61B 3/00* (2006.01)

(52) U.S. Cl. .................. 351/205; 351/221; 351/246

(58) Field of Classification Search ............... 351/205, 351/221, 222, 243, 246, 241
See application file for complete search history.

(56) References Cited

U.S. PATENT DOCUMENTS

| | | | |
|---|---|---|---|
| 4,074,361 A | * | 2/1978 | Clow .......................... 708/191 |
| 4,579,430 A | | 4/1986 | Bille |
| 4,723,845 A | * | 2/1988 | Mizutani et al. ............ 356/623 |
| 5,062,702 A | | 11/1991 | Bille |
| 5,161,059 A | | 11/1992 | Swanson et al. |
| 5,764,341 A | | 6/1998 | Fujieda et al. |
| 5,772,298 A | | 6/1998 | Miyake |
| 6,050,687 A | | 4/2000 | Bille et al. |
| 2003/0071969 A1 | | 4/2003 | Levine et al. |

FOREIGN PATENT DOCUMENTS

| | | |
|---|---|---|
| EP | 1419752 A1 | 5/2004 |
| WO | 02087428 A2 | 11/2002 |
| WO | 2006114468 A1 | 11/2006 |

OTHER PUBLICATIONS

Acosta Eva et al., "Variable aberration generators using rotated Zernike plates" J Opt Soc Am A; Journal of the Optical Society of America A:Optics and Image Science, and Vision, Sep. 2005 (2005-2009), pp. 1993-1996.

* cited by examiner

*Primary Examiner*—Ricky L Mack
*Assistant Examiner*—Brandi N Thomas
(74) *Attorney, Agent, or Firm*—Nydegger & Associates

(57) ABSTRACT

A device to compensate for asymmetrical aberrations in a beam of light includes at least one dual compensator positioned on the beam path. Structurally, the dual compensator includes two juxtaposed plates, each having a same pattern presented thereon. The patterns, however, are rotated through an angle α relative to each other. Together, the plates of the dual compensator can then be rotated on the beam path through an angle β to compensate for asymmetrical aberrations in the light beam. Dual compensators, having appropriate patterns, can be collectively used to compensate for astigmatism, coma and trefoil.

17 Claims, 3 Drawing Sheets

ADAPTIVE OPTICS FOR COMPENSATING FOR OPTICAL ABERRATIONS IN AN IMAGING PROCESS

This application is a continuation-in-part of application Ser. No. 10/718,406, filed Nov. 20, 2003, now U.S. Pat. No. 7,510,283 which is currently pending. The contents of application Ser. No. 10/718,406 are incorporated herein by reference.

FIELD OF THE INVENTION

The present invention pertains generally to systems for correcting optical imaging. More particularly, the present invention pertains to systems that compensate for optical aberrations when they are introduced into a light beam by a human eye. The present invention is particularly, but not exclusively, useful as a system and device that compensates for the lower order asymmetrical aberrations in an eye, such as astigmatism, coma and trefoil.

BACKGROUND OF THE INVENTION

In vision science it is common to represent errors of the eye as wavefront aberrations. When doing this, there are various kinds of mathematical representations that can be used. In particular, polynomials, such as the Zernike polynomials, are well suited for this purpose and are frequently used. In general, the Zernike polynomials describe defects that are departures from perfect imagery. More specifically, they describe the properties of an aberrated wavefront, and do so without regard to the symmetrical properties of the system that gave rise to the wavefront.

Mathematically, the Zernike polynomials are usually defined in polar coordinates $Z(\rho,\theta)$, where $\rho$ is the radial coordinate ranging from 0 to 1, and $\theta$ is the azimuthal component ranging from 0 to $2\pi$. Typically, each Zernike polynomial consists of three components. These are: a normalization factor, a radial dependent component, and an azimuthal dependent component. In this context, the radial component is a polynomial, whereas the azimuthal component is sinusoidal.

With the above in mind, a wavefront description using Zernike polynomials can be given in the general form:

$$W(\rho,\theta) = \Sigma c_{nm} Z_{nm}(\rho,\theta,\alpha_{nm})$$

In the above expression, "n" pertains to the order of the polynomial (i.e. $2^{nd}$ or $3^{rd}$ order aberration) and "m" pertains to frequency (i.e. $\theta$, $2\theta$, and $3\theta$). Further, $c_{nm}$ is a coefficient that pertains to magnitude; and $Z_{nm}(\rho,\theta,\alpha_{nm})$ depends on radial and azimuthal considerations as they relate to a particular axis ($\alpha_{nm}$).

When considering the human eye as a genuine optical system, aberrations can be generally categorized as being either symmetric or asymmetric with respect to the optical axis of the eye. For this categorization, symmetrical aberrations are radially symmetrical with respect to the optical axis, while the asymmetrical aberrations are not. As indicated by the Zernike polynomials, in addition to their symmetry or lack thereof the various optical aberrations of the eye can be categorized by their order. Insofar as imaging is concerned, it happens that the so-called lower order aberrations (i.e. $2^{nd}$, $3^{rd}$ and $4^{th}$ order) can be significantly detrimental. These lower order aberrations include both symmetrical and asymmetrical aberrations.

Perhaps, the most well known aberrations of a human eye are myopia, hyperopia and astigmatism. All are $2^{nd}$ order aberrations, according to the Zernike polynomials, but of these, only astigmatism is an asymmetrical aberration. Heretofore, these aberrations have been corrected by glasses, contact lenses, or eximer-laser-surgery, without directly considering the effects of other aberrations. Along with the $2^{nd}$ order aberrations just mentioned, however, additional asymmetrical aberrations in the $3^{rd}$ and $4^{th}$ orders can also be significantly detrimental to human vision. This is particularly so under relatively poor lighting conditions. Indeed, aside from the effects caused by myopia and hyperopia, it is estimated that of the remaining detrimental effect on vision, 85% is caused by the $2^{nd}$ and $3^{rd}$ order asymmetrical aberrations (i.e. astigmatism, coma and trefoil), 10% is caused by the symmetrical $4^{th}$ order spherical aberration, while only about 5% result from the remaining higher order aberrations. In any event, when vision correction is undertaken, it is clear that a compensation for as many aberrations as possible would be beneficial.

With the above in mind, the aberrations of interest here are the asymmetrical aberrations that include: astigmatism ($Z_3$ and $Z_5$; $2^{nd}$ order), coma ($Z_7$ and $Z_8$; $3^{rd}$ order) and trefoil ($Z_6$ and $Z_9$; $3^{rd}$ order). Using the Zernike polynomials, each asymmetrical aberration can be modeled individually for each patient. Importantly, this modeling can be done as pairs of identical patterns. Further, the pair of patterns for a particular asymmetrical aberration (e.g. coma) are patient specific. In each instance, the patterns for a particular asymmetrical aberration will have a common orthogonal axis. Each pattern, however, will have a different rotational alignment around this common axis. Stated differently, there will be an angle of rotation "$\alpha$" between the patterns of an asymmetrical aberration. Again, the angle "$\alpha$" will be patient specific and it will determine the magnitude of the aberration. Thus, for each patient, a model for each asymmetrical aberration (e.g. astigmatism, coma, and trefoil) will have respective patterns, and will have a respective angle "$\alpha$" between the patterns.

In light of the above it is an object of the present invention to provide adaptive optics that model asymmetrical aberrations of the eye in accordance with appropriate Zernike polynomials to compensate for the asymmetrical aberrations that are introduced by a human eye in an imaging process. Yet another object of the present invention is to provide an optical device that helps minimize the detrimental effects on vision that are caused by asymmetrical aberrations induced by a human eye. Still another object of the present invention is to compensate for asymmetrical aberrations by providing adaptive optics that are easy to use, simple to assemble, and comparatively cost effective.

SUMMARY OF THE INVENTION

In accordance with the present invention, a device is provided as an adaptive optics unit to compensate for asymmetrical aberrations in a beam of light. To operationally orient the components of the device for this purpose, the light beam is considered to be directed along a beam path axis. Using the beam path axis as a reference, a plurality of dual compensators are positioned sequentially along the beam path, and are substantially centered thereon. Additionally, the device includes a mechanical apparatus for individually rotating each dual compensator about the beam path axis through a respective angle $\beta$. Doing this, each dual compensator is thereby able to compensate for a particular asymmetrical aberration in the light beam.

In detail, each dual compensator comprises two flat plates that are shaped as circular disks. Preferably, each plate is made of glass, and it has a thickness of approximately one millimeter and a diameter of approximately ten millimeters. Each plate has a substantially flat surface with a same pattern presented thereon. As intended for the present invention, these patterns are created on the surfaces of the plates by a sodium ion bombardment process that is well known in the pertinent art. Importantly, the patterns in a dual compensator correspond to the Zernike polynomials of the asymmetrical aberration (e.g. $Z_7$ and $Z_8$ for coma) that is to be compensated for by the dual compensator. Further, each pattern has a central point, and each pattern defines a pattern axis on the surface of the plate.

For their assembly, the plates of a dual compensator are juxtaposed, and their respective central points are positioned on the beam path axis. Further, their respective pattern axes are oriented substantially perpendicular to the beam path axis. In accordance with diagnostic data obtained from the patient, the respective pattern axes in a dual compensator are rotated through an angle "$\alpha$" relative to each other. Once the angle "$\alpha$" has been established, the plates of a dual compensator are then rotated, together in combination, about the beam path axis. This rotation, through an angle "$\beta$", is done to compensate for the asymmetrical aberrations. For this assembly, both the angle "$\alpha$" and the angle "$\beta$" are patient specific.

For a device of the present invention, as indicated above, a separate dual compensator is provided for each asymmetrical aberration. For example, to compensate for astigmatism, coma and trefoil, three different dual compensators will be required. One dual compensator will be specifically configured to compensate for astigmatism, another will be configured to compensate for coma, and yet another will be configured to compensate for trefoil. Specifically, the dual compensator for astigmatism will have patient specific astigmatism patterns ($Z_3$ and $Z_5$) with an angle $\alpha_1$, between its respective pattern axes to compensate for astigmatism. Similarly, the dual compensator for coma will have patient specific coma patterns ($Z_7$ and $Z_8$) with an angle $\alpha_2$ between these respective pattern axes to compensate for coma. And, a dual compensator for trefoil will have patient specific trefoil patterns ($Z_6$ and $Z_9$) with an angle $\alpha_3$ between the pattern axes to compensate for trefoil. As noted above, each dual compensator will then need to be individually rotated about the beam path axis. Specifically these rotations will respectively be through angles $\beta_1$, $\beta_2$, and $\beta_3$.

It is envisioned for the present invention that asymmetrical aberrations, other than astigmatism, coma and trefoil as mentioned above, can also be corrected. Specifically, dual compensators for asymmetrical aberrations of the $4^{th}$ order, and higher, can be assembled and used in a same manner as indicated above.

An intended application for the device of the present invention is as an aberration compensator in an imaging system that is to be used for ophthalmic laser surgery. Typically, such systems incorporate a MEMS mirror to compensate for the higher order aberrations and the symmetrical aberrations associated with myopia, hyperopia and spherical aberration. When used in such a system, in combination with a MEMS mirror, the present invention is able to reduce the compensation burden that would otherwise be required by the MEMS mirror acting alone. In particular, this will be so when compensation for asymmetrical aberrations is desired.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
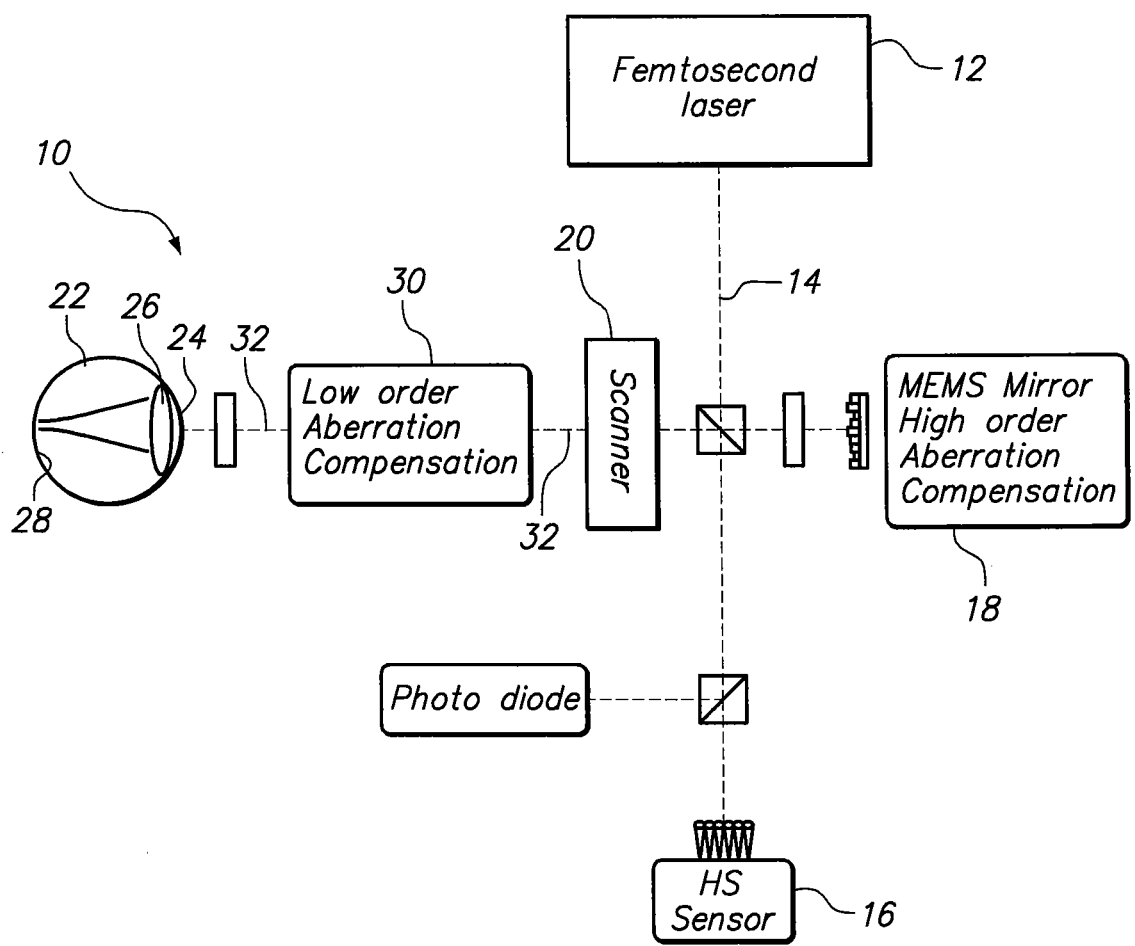
FIG. 1 is a schematic of an imaging system that incorporates a unit to compensate for asymmetrical aberrations in accordance with the present invention.

Referring initially to FIG. 1, an optical system for incorporating the present invention is shown and generally designated 10. As shown, the system 10 includes a laser source 12 for generating a laser beam 14. Through electronic connections, not shown in FIG. 1, this laser beam 14 is then monitored by a sensor 16 (preferably a Hartmann Shack type sensor), it is also refined by a MEMS mirror 18 that removes certain aberrations from the laser beam 14, and it is controlled by a scanner 20. More specifically, the scanner 20 can be preprogrammed to direct the laser beam 14 toward an eye 22 for various purposes. Specifically, the eye 22 has a cornea 24, a lens 26 and a retina 28 that can be imaged or be operated on by a surgical laser beam 14. FIG. 1 also shows that a compensation device 30 is positioned between the scanner 20 and the eye 22, and that the laser beam 14 will pass through the compensation device 30 along a beam path axis 32.

Figure 2:
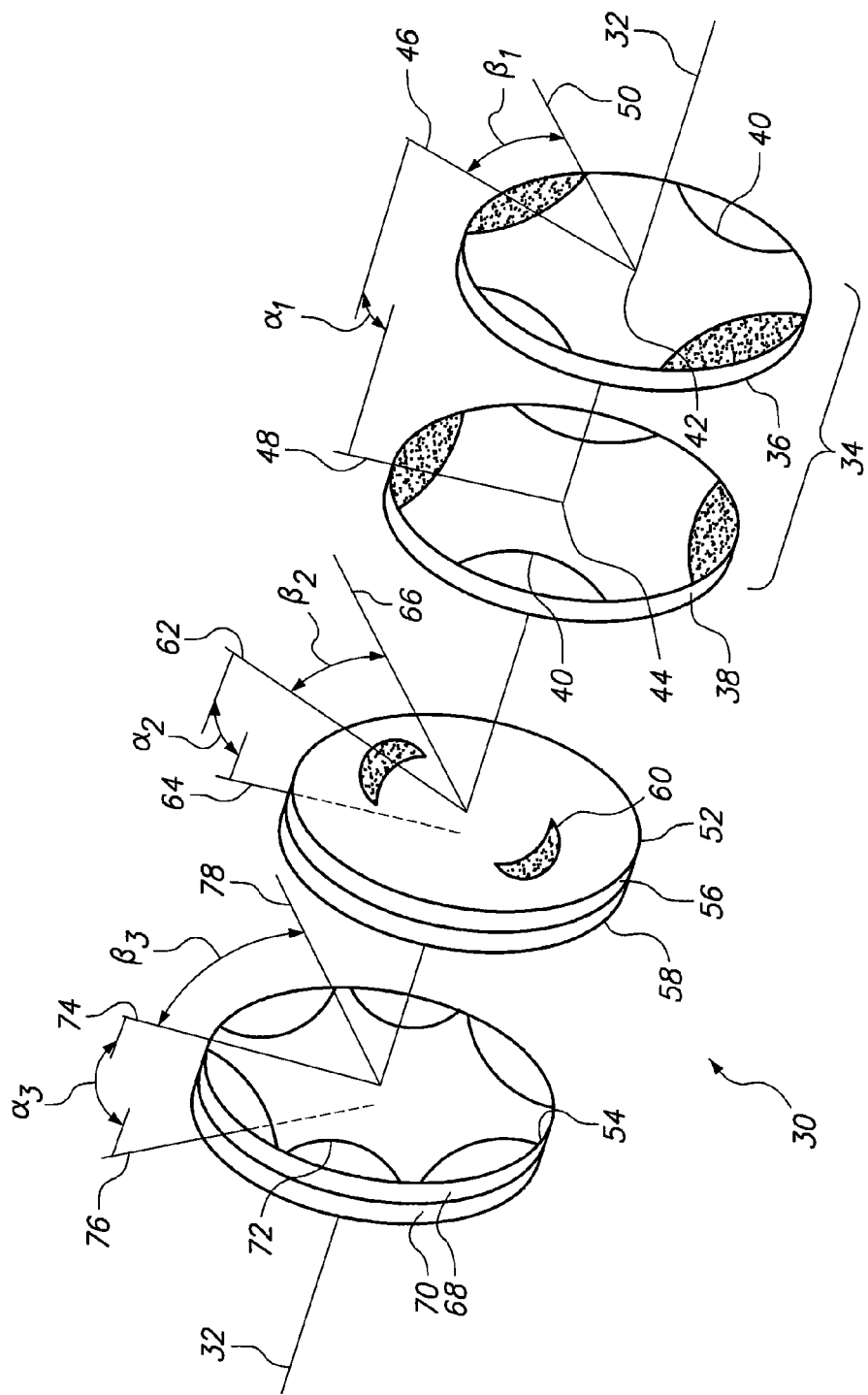
FIG. 2 is an exploded view of dual compensators aligned along a beam path axis to compensate for asymmetrical aberrations in accordance with the present invention.
Figure 3:
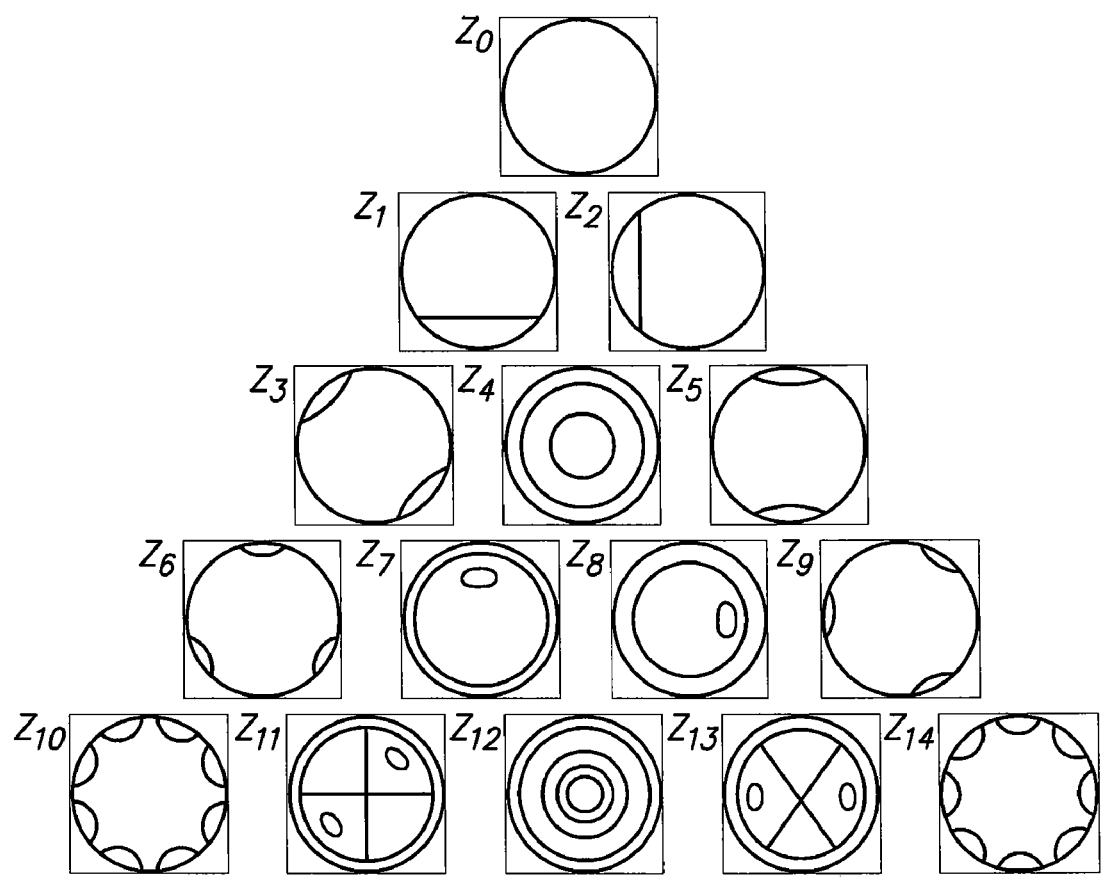
FIG. 3 is a presentation of patterns in accordance with Zernike polynomials for use with the present invention.

Referring now to FIG. 2 it will be seen that the device 30 includes a dual compensator 34 having two circular, disk-shaped plates; a plate 36 and a plate 38. As envisioned for the present invention, each of the plates 36 and 38 will be made of glass, will have a thickness of about one millimeter and will have a diameter of about ten millimeters. Further, each of the plates 36 and 38 will have a same pattern 40 presented on one of its respective surfaces. The pattern 40 on plate 36 will have a center point 42, and the pattern 40 on plate 38 will have a center point 44. Also, the pattern 40 on plate 36 will define a pattern axis 46, and the pattern 40 on plate 38 will define an identical pattern axis 48. Preferably, the pattern 40 is created by sodium ion bombardment in a manner well known in the pertinent art. In any event, the pattern 40 that is created on the surfaces of the plates 36 and 38 will model an appropriate Zernike polynomial. For example, the pattern 40 shown for the dual compensator 34 is intended to model the Zernike polynomials $Z_3$ and $Z_5$ for astigmatism that are represented in FIG. 3. For astigmatism:

| | Astigmatism | | |
|---|---|---|---|
| Zernike Polynomial | Normalization Factor | Polar Coordinates | Axis |
| $Z_3$ | $\sqrt{6}$ | $\rho^2 \sin 2\theta$ | axis at 45° |
| $Z_5$ | $\sqrt{6}$ | $\rho^2 \cos 2\theta$ | axis at 0° or 90° |

The assembly of the dual compensator 34 is accomplished by juxtaposing the plates 36 and 38. For this juxtaposition, it is important that the plate 36 be rotated through an angle "$\alpha_1$" relative to the plate 38. This angle, "$\alpha_1$", is patient specific and is determined from diagnostic data. It is also a measure of the magnitude of the amount of astigmatism involved. Once the angle "$\alpha_1$" is determined, the juxtaposed plates 36 and 38 are then positioned on the beam path axis 32 with their respective center points 42 and 44 located on the beam path axis 32. The now assembled and properly positioned dual compensator 34 can then be subsequently rotated about the beam path axis 32 through an angle "$\beta_1$", as required. For purposes of this disclosure, the angle "$\beta_1$" is measured from a base line 50 that is perpendicular to the beam path axis 32. Specifically, this rotation through the angle "$\beta_1$" is done to properly orient the dual compensator 34 for the particular patient. With the angles "$\alpha_1$" and "$\beta_1$" properly established, the dual compensator 34 will compensate for any asymmetrical aberration of astigmatism that may be present in the laser beam 14 after it has been reflected from the eye 22 of the patient.

In addition to the dual compensator 34, the device 30 may also include a dual compensator 52 to compensate for coma, and a dual compensator 54 to compensate for trefoil. Like the dual compensator 34, the dual compensator 52 includes two plates; a plate 56 and a plate 58. These plates 56 and 58 respectively present a pattern 60 that corresponds to the Zernike polynomials $Z_7$ and $Z_8$ represented in FIG. 3 for the asymmetrical aberration coma. For coma:

| | | Coma | |
|---|---|---|---|
| Zernike Polynomial | Normalization Factor | Polar Coordinates | Axis |
| $Z_7$ | $\sqrt{8}$ | $(3\rho^3 - 2\rho)\sin\theta$ | along x axis |
| $Z_8$ | $\sqrt{8}$ | $(3\rho^3 - 2\rho)\cos\theta$ | along y axis |

When juxtaposed and assembled, the plates 56 and 58 define respective pattern axes 62 and 64 that are offset from each other by an angle "$\alpha_2$". As shown, the assembled dual compensator 52 can then be rotated through and angle "$\beta_2$" relative to a base line 66 to compensate for coma. In this case, the base line 66 is parallel to the base line 50 that is used to measure a rotation of the dual compensator 34.

Similar to the compensators 34 and 52, the dual compensator 54 includes two plates; a plate 68 and a plate 70. These plates 68 and 70 respectively present a pattern 72 that corresponds to the Zernike polynomials $Z_6$ and $Z_9$ represented in FIG. 3 for the asymmetrical aberration trefoil. For trefoil:

| | | Trefoil | |
|---|---|---|---|
| Zernike Polynomial | Normalization Factor | Polar Coordinates | Axis |
| $Z_6$ | $\sqrt{8}$ | $\rho^3\sin3\theta$ | axis at 30° |
| $Z_9$ | $\sqrt{8}$ | $\rho^3\cos3\theta$ | axis at 0° |

When juxtaposed and assembled, the plates 68 and 70 define respective pattern axes 74 and 76 that are offset from each other by an angle "$\alpha_3$". As shown, the assembled dual compensator 54 can then be rotated through and angle "$\beta_3$" relative to a base line 78 to compensate for trefoil. In this case, the base line 78 is parallel to the base lines 66 and 50 that are used to measure rotations of the dual compensators 34 and 52.

While the particular Adaptive Optics for Compensating for Optical Aberrations in an Imaging Process as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for use in an optical system to compensate for asymmetrical aberrations in a beam of light, wherein the light beam is directed along a beam path, with the beam path defining an axis and said system comprising:

at least one dual compensator positioned on the beam path and substantially centered thereon wherein said dual compensator comprises a first plate having a substantially flat surface with a pattern presented thereon, wherein the pattern has a central point and defines a pattern axis in the surface of said plate and a second plate having a substantially flat surface with a same pattern presented thereon, wherein the central point of said first plate and the central point of said second plate are positioned on the beam path axis with the respective pattern axes substantially perpendicular to the beam path axis, and further wherein the pattern axis of said first plate is rotated through an angle α relative to the pattern axis of said second plate; and a means for rotating said dual compensator about the axis of the beam path through an angle β to compensate for asymmetrical aberrations in the light beam.

2. A device as recited in claim 1 wherein said first plate and said second plate are shaped as circular disks having a thickness of approximately one millimeter and a diameter of approximately ten millimeters.

3. A device as recited in claim 2 wherein said first plate and said second plate are made of glass.

4. A device as recited in claim 3 wherein the pattern on the surface of said first plate and the pattern on the surface of said second plate are created by ion bombardment.

5. A device as recited in claim 1 wherein said system includes a plurality of dual compensators comprising:

a first dual compensator having first patterns to compensate for astigmatism;

a second dual compensator having second patterns to compensate for coma; and a third dual compensator having third patterns to compensate for trefoil.

6. A device as recited in claim 1 further comprising a laser unit for generating the light beam, wherein the light beam is a laser beam.

7. A device as recited in claim 6 wherein the laser beam is used for retinal imaging in laser surgery.

8. A device as recited in claim 7 wherein the system further comprises a MEMS mirror for concerted use with the dual compensator to minimize optical aberrations in the light beam.

9. An imaging system for use during ophthalmic laser surgery which comprises:

a laser unit for generating a laser beam, wherein the laser beam defines a beam path having an axis;

a plurality of dual compensators sequentially positioned along the beam path axis and substantially centered thereon wherein each said dual compensator comprises a first plate having a substantially flat surface with a pattern presented thereon, wherein the pattern has a central point and defines a pattern axis in the surface of said plate and a second plate having a substantially flat surface with a same pattern presented thereon, wherein the central point of said first plate and the central point of said second plate are positioned on the beam path axis with the respective pattern axes substantially perpendicular to the beam path axis, and further wherein the pattern axis of said first plate is rotated through an angle α relative to the pattern axis of said second plate; and a means for selectively rotating each said dual compensator about the beam path axis to compensate for aberrations in the light beam during surgery.

10. A system as recited in claim 9 wherein said plurality of dual compensators comprise:
   a first dual compensator having first patterns with an angle $\alpha_1$ between the pattern axes to compensate for astigmatism;
   a second dual compensator having second patterns with an angle $\alpha_2$ between the pattern axes to compensate for coma; and
   a third dual compensator having third patterns with an angle $\alpha_3$ between the pattern axes to compensate for trefoil.

11. A system as recited in claim 10 wherein said first dual compensator is rotated about the beam path axis through an angle $\beta_1$, wherein said second dual compensator is rotated about the beam path axis through an angle $\beta_2$, and wherein said third dual compensator is rotated about the beam path axis through an angle $\beta_3$, to compensate for asymmetrical aberrations in the laser beam.

12. A system as recited in claim 9 wherein said first plate and said second plate are shaped as circular disks having a thickness of approximately one millimeter and a diameter of approximately ten millimeters.

13. A system as recited in claim 9 wherein said first plate and said second plate are made of glass and the pattern on the surface of said first plate and the pattern on the surface of said second plate are created by ion bombardment 14. A method for assembling a system to compensate for asymmetrical aberrations introduced into a laser beam, wherein the laser beam defines a beam path axis and said method comprises the steps of:
   positioning a plurality of dual compensators in alignment along the beam path axis wherein each said dual compensator comprises a first plate having a substantially flat surface with a pattern presented thereon, wherein the pattern has a central point and defines a pattern axis in the surface of said plate and a second plate having a substantially flat surface with a same pattern presented thereon, wherein the central point of said first plate and the central point of said second plate are positioned on the beam path axis with the respective pattern axes substantially perpendicular to the beam path axis, and further wherein the pattern axis of said first plate is rotated through an angle α relative to the pattern axis of said second plate; and
   coupling a rotating means with each of the dual compensators for selectively rotating each dual compensator about the beam path axis through an angle β to compensate for asymmetrical aberrations in the light beam.

15. A method as recited in claim 14 wherein the plurality of dual compensators comprise:
   a first dual compensator having first patterns with an angle $\alpha_1$ between the respective pattern axes to compensate for astigmatism;
   a second dual compensator having second patterns with an angle $\alpha_2$ between the respective pattern axes to compensate for coma; and
   a third dual compensator having third patterns with an angle $\alpha_3$ between the respective pattern axes to compensate for trefoil.

16. A method as recited in claim 15 further comprising the steps of:
   rotating the first dual compensator about the axis of the beam path through an angle $\beta_1$;
   rotating the second dual compensator about the axis of the beam path through an angle $\beta_2$; and
   rotating the third dual compensator about the axis of the beam path through an angle $\beta_3$, to collectively compensate for asymmetrical aberrations in the laser beam.

17. A method as recited in claim 14 wherein said first plate and said second plate are shaped as circular disks having a thickness of approximately one millimeter and a diameter of approximately ten millimeters, and further wherein the first plate and the second plate are made of glass and the pattern on the surface of said first plate and the pattern on the surface of said second plate are created by ion bombardment.

* * * * *